United States Patent
Tanedani

(10) Patent No.: US 9,028,854 B2
(45) Date of Patent: May 12, 2015

(54) PESTICIDAL COMPOSITION

(75) Inventor: Toshiyuki Tanedani, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1200 days.

(21) Appl. No.: 11/299,620

(22) Filed: Dec. 13, 2005

(65) Prior Publication Data

US 2006/0129021 A1    Jun. 15, 2006

(30) Foreign Application Priority Data

Dec. 14, 2004   (JP) ................................. 2004-360988

(51) Int. Cl.
*A01N 43/40* (2006.01)
*A01N 25/30* (2006.01)
*A01N 25/04* (2006.01)

(52) U.S. Cl.
CPC ...................................... *A01N 43/40* (2013.01)

(58) Field of Classification Search
USPC ............... 424/405, 43, 44, 45; 514/277, 345; 546/314; 588/402, 405, 408, 409
See application file for complete search history.

(56) References Cited

U.S. PATENT DOCUMENTS

| | | | |
|---|---|---|---|
| 2,539,269 A * | 1/1951 | Parr ............................... | 514/750 |
| 4,751,225 A | 6/1988 | Nishida et al. | |
| 4,871,766 A | 10/1989 | Tsuda et al. | |
| 5,674,517 A * | 10/1997 | Carpenter ..................... | 424/405 |
| 6,232,328 B1 | 5/2001 | Dorn et al. | |
| 6,296,864 B1 * | 10/2001 | Zen ............................... | 424/405 |
| 6,468,555 B1 | 10/2002 | Nakamura | |
| 2005/0042245 A1 * | 2/2005 | Taranta et al. ................ | 424/405 |

FOREIGN PATENT DOCUMENTS

| | | |
|---|---|---|
| EP | 0 839 448 | 5/1998 |
| JP | 7-285803 | 10/1995 |
| JP | 07-285803 | 10/1995 |
| JP | 10-120502 | 5/1998 |

OTHER PUBLICATIONS

"Emulsifiable Concentrates", Kaiser Industries Ltd., 2004 [online], [retrieved Jan. 14, 2014], Retrieved from the Internet: <URL: http://www.kaiserindustries.com/emulsifiable-concentrate.php>.*
Office Action in corresponding Brazilian patent application PI 0505513-0 dated Oct. 29, 2013 with English translation.
Taiwanese Search Report issued May 4, 2011 in corresponding Taiwan Patent Application No. 094142894.

* cited by examiner

*Primary Examiner* — Jane C Oswecki
(74) *Attorney, Agent, or Firm* — Wenderoth, Lind & Ponack, L.L.P.

(57) ABSTRACT

A pesticidal composition comprising 4-phenoxyphenyl 2-(2-pyridyloxy)propyl ether; a hydrophobic organic solvent capable of dissolving 0.1-fold by weight of 4-phenoxyphenyl 2-(2-pyridyloxy)propyl ether at 0° C.; polyvinyl alcohol; a nonionic surfactant selected from the group consisting of alkoxylated castor oil, alkoxylated hydrogenated castor oil and alkoxylated hydrogenated castor oil fatty acid ester; and water, is excellent in storage stability.

14 Claims, No Drawings

PESTICIDAL COMPOSITION

BACKGROUND OF THE INVENTION

1. Field of the Invention

The present invention relates to a pesticidal composition containing pyriproxyfen as an active ingredient.

2. Description of the Related Art

4-Phenoxyphenyl 2-(2-pyridyloxy)propyl ether (hereinafter, referred to as pyriproxyfen) is a compound having a pest control activity (see U.S. Pat. No. 4,751,225). Moreover, an emulsifiable concentrate containing pyriproxyfen (see, for example, U.S. Pat. No. 6,296,864) and an oil-in-water emulsion containing pyriproxyfen (see, for example, JP-7-285803A) are known.

SUMMARY OF THE INVENTION

The present invention provides a pesticidal composition which is excellent in preparation stability by combining pyriproxyfen, polyvinyl alcohol and a nonionic surfactant selected from the group consisting of alkoxylated castor oil, alkoxylated hydrogenated castor oil and alkoxylated hydrogenated castor oil fatty acid ester (hereinafter, referred to as the present nonionic surfactant).

That is, the present invention provides a pesticidal composition comprising pyriproxyfen, a hydrophobic organic solvent capable of dissolving 0.1-fold by weight of pyriproxyfen at 0° C., polyvinyl alcohol, the present nonionic surfactant and water, wherein a weight ratio of pyriproxyfen and water is in the range from 1:20 to 1:3.

The pesticidal composition of the present invention usually has a form of EW formulation (emulsion, oil in water), is excellent in preparation stability, and the pesticidal composition can be expected that it has a stable performance even after it has been stored over a long term.

DETAILED DESCRIPTION OF THE PREFERRED EMBODIMENTS

Pyriproxyfen used in the present invention may be manufactured, for example, by a method described in U.S. Pat. No. 4,751,225. Moreover, a commercially available product of pyriproxyfen may be also used.

A hydrophobic organic solvent capable of dissolving 0.1-fold by weight of pyriproxyfen at 0° C. used in the present invention (hereinafter, referred to as the present hydrophobic organic solvent) means a hydrophobic organic solvent which gives a stable and uniform solution even in the case where after the mixture of one part by weight of the present hydrophobic organic solvent and 0.1 part by weight of pyriproxyfen was agitated, heated if it is necessary, and dissolved, then, it was cooled to 0° C. The present hydrophobic organic solvent preferably has a 100 ppm or less of solubility in water at 20° C.

Examples of the present hydrophobic organic solvent used in the present invention include a benzene-based hydrocarbon solvent such as toluene, xylene, tetramethylbenzene, 1,1-diphenylmethane, diphenylethane, 1,1-ditolylethane, 1-phenyl-1-xylylethane, 1-phenyl-1-(ethylphenyl)ethane, 1-xylyl-1-(α-methylbenzylphenyl)ethane, bis(α-methylbenzyl)xylene and the like; a naphthalene-based hydrocarbon solvent such as methylnaphthalene, dimethylnaphthalene, dimethyl isopropylnaphthalene and the like; an aromatic ester-based solvent such as phenyl acetate, benzyl acetate, tolyl acetate, 4-phenylbutyl acetate, methyl benzoate, ethyl benzoate, propyl benzoate, butyl benzoate, isoamyl benzoate and the like; an aliphatic ester-based solvent such as butyl propionate, isoamyl propionate, ethyl butyrate, butyl butyrate, isoamyl butyrate, isoamyl isovalerate, methyl laurate and the like; a vegetable oil such as soybean oil, corn oil, rapeseed oil and the like. In the present invention, the benzene-based hydrocarbon solvent and the naphthalene-based hydrocarbon solvent are preferably used.

The present hydrophobic organic solvent used in the present invention includes the above-described single organic solvent and a mixture of the above-described organic solvents.

An organic solvent which is commercially available may be used as the present hydrophobic organic solvent as it is in the present invention. Examples of the organic solvent which is commercially available include Hisol SAS-296 (mixture of 1-pheny-1-xylylethane and 1-phenyl-1-ethylphenylethane, product name of Nippon Oil Co., Ltd.), Hisol SAS-LH (product name of Nippon Oil Co., Ltd.), Cactus solvent HP-MN (methylnaphthalene 80%, product name of Japan Energy Corporation), Cactus solvent HP-DMN (dimethylnaphthalene 80%, product name of Japan Energy Corporation), Cactus solvent P-180 (mixture of methylnaphthalene and dimethylnaphthalene, product name of Japan Energy Corporation), Cactus solvent P-200 (mixture of methylnaphthalene and dimethylnaphthalene, product name of Japan Energy Corporation), Cactus solvent P-220 (mixture of methylnaphthalene and dimethylnaphthalene, product name of Japan Energy Corporation), Cactus solvent PAD-1 (dimethyl monoisopropylnaphthalene, product name of Japan Energy Corporation), Solvesso 200 (aromatic hydrocarbon, product name of ExxonMobil Chemical Corporation), Swazol 100 (toluene, product name of Maruzen Petroleum Inc.), and Swazol 200 (xylene, product name of Maruzen Petroleum Inc.). Moreover, these organic solvents which are commercially available may be also used as a mixture.

A content amount of the present hydrophobic organic solvent in the present invention may be properly determined depending upon an easiness of manufacturing the composition of the present invention, a purpose of use of the composition of the present invention and the like, but usually, it is contained in the composition of the present invention in the range from 5 to 30% by weight, and more preferably in the range from 10 to 20% by weight.

Polyvinyl alcohol used in the present invention means a polymer compound which can be obtained by saponifying polyvinyl acetate obtained by polymerizing vinyl acetate with alkali, acid, ammonia or the like. Referring to polyvinyl alcohol, its physical properties are varied depending upon its degree of polymerization and degree of saponification. In the present invention, it is preferable that as for polyvinyl alcohol, the viscosity of 4% by weight of aqueous solution is in the range from 1 to 70 mPa at 20° C. and its degree of saponification is in the range from 70 to 100% by mole. It is more preferable that as for polyvinyl alcohol, the viscosity of 4% by weight of aqueous solution is 40 mPa·s or less at 20° C., and its degree of saponification is 90% by mole or less. For the present invention, as polyvinyl alcohol, a product which is commercially available may be used as it is, and examples of such polyvinyl alcohol include GOHSENOL GL-05 (product name of Nippon Synthetic Chemical Industry, Co., Ltd.), GOHSENOL GL-03 (product name of Nippon Synthetic Chemical Industry, Co., Ltd.) and GOHSENOL KL-05 (product name of Nippon Synthetic Chemical Industry, Co., Ltd.).

A content amount of polyvinyl alcohol in the present invention is usually in the range from 0.5 to 4% by weight, and preferably in the range from 1 to 3% by weight in the composition of the present invention.

Alkoxylated castor oil in the present nonionic surfactant used in the present invention is a compound which is obtained by performing an addition polymerization of alkylene oxide having carbon atoms of 2-4 (for example, ethylene oxide, propylene oxide) to castor oil in the presence of a base, and examples thereof include ethoxylated castor oil in which the addition polymerization of ethylene oxide is performed to castor oil, and ethoxylated propoxylated castor oil in which a random or block polymerization of ethylene oxide and propylene oxide is performed to castor oil. Alkoxylated hydrogenated castor oil is a compound which is obtained by performing, in the presence of the base, the addition polymerization of alkylene oxide having carbon atoms of 2-4 (for example, ethylene oxide, propylene oxide) to hydrogenated castor oil (so-called hardened castor oil) which is obtained by hydrogenating castor oil, and examples thereof include ethoxylated hydrogenated castor oil in which the addition polymerization of ethylene oxide is performed to hydrogenated castor oil and ethoxylated propoxylated hydrogenated castor oil in which the random or block polymerization of ethylene oxide and propylene oxide is performed to hydrogenated castor oil. Alkoxylated hydrogenated castor oil fatty acid ester is a mono or tri-ester obtained by performing an esterification of alkoxylated hydrogenated castor oil and a fatty acid (for example, isostearic acid, lauric acid), and examples thereof include ethoxylated hydrogenated castor oil fatty acid ester.

A compound obtained by adding ethylene oxide to a triglyceride of ricinolic acid, which is a major component of castor oil, has a structure represented by the following formula:

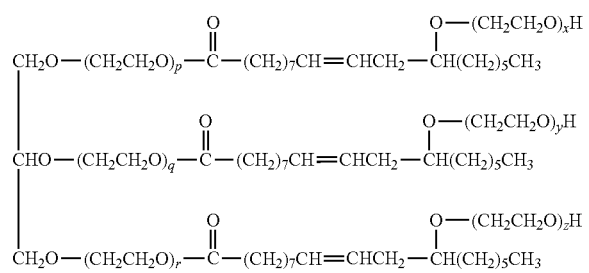

[wherein, each of p, q and r represents an integer of 0 or more, and each of x, y and z represents an integer of 1 or more].

Examples of ethoxylated castor oil which is commercially available include Alkamulus R81 (product name of Rhodia, Co, Ltd.), Alkamulus BR (product name of Rhodia, Co, Ltd.), Alkamulus OR/40 (product name of Rhodia, Co, Ltd.), Alkamulus 14R (product name of Rhodia, Co, Ltd.), Sorpol CA30 (product name of Toho Chemical Industry, Co., Ltd.), Sorpol CA42 (product name of Toho Chemical Industry Co., Ltd.), CO-20TX (additional number of moles of ethylene oxide: 20, product name of Nikko Chemicals, Co., Ltd.), CO-40TX (additional number of moles of ethylene oxide: 40, product name of Nikko Chemicals, Co., Ltd.), CO-50TX (additional number of moles of ethylene oxide: 50, product name of Nikko Chemicals, Co., Ltd.), CO-60TX (additional number of moles of ethylene oxide: 60, product name of Nikko Chemicals, Co., Ltd.), Etocas 29 (additional number of moles of ethylene oxide: 29, product name of Croda Japan KK), Etocas 35 (additional number of moles of ethylene oxide: 35, product name of Croda Japan KK), Etocas 40 (additional number of moles of ethylene oxide: 40, product name of Croda Japan KK), Etocas 60 (additional number of moles of ethylene oxide: 60, product name of Croda Japan KK), EMALEX C-20 (additional number of moles of ethylene oxide: 20, product name of Nihon Emulsion Co., Ltd.), EMALEX C-30 (additional number of moles of ethylene oxide: 30, product name of Nihon Emulsion Co., Ltd.), and EMALEX C-40 (additional number of moles of ethylene oxide: 40, product name of Nihon Emulsion Co., Ltd.). Examples of ethoxylated hydrogenated castor oil which is commercially available include Croduret 7 (product name of Croda Japan KK), Croduret 25 (product name of Croda Japan KK), Croduret 40 (product name of Croda Japan KK), Croduret 50 (product name of Croda Japan KK), Croduret 60 (product name of Croda Japan KK), HCO-20 (additional number of moles of ethylene oxide: 20, product name of Nikko Chemicals, Co., Ltd.), HCO-30 (additional number of moles of ethylene oxide: 30, product name of Nikko Chemicals, Co., Ltd.), HCO-40 (additional number of moles of ethylene oxide: 40, product name of Nikko Chemicals, Co., Ltd.), EMALEX HC-20 (additional number of moles of ethylene oxide: 20, product name of Nihon Emulsion Co., Ltd.) and the like. Examples of ethoxylated hydrogenated castor oil fatty acid ester which is commercially available include EMALEX RWIS-158 (ethoxylated hydrogenated castor oil monoisostearate, additional number of moles of ethylene oxide: 58, product name of Nihon Emulsion Co., Ltd.), EMALEX RWIS-360 (ethoxylated hydrogenated castor oil triisostearate, additional number of moles of ethylene oxide: 60, product name of Nihon Emulsion Co., Ltd.), and EMALEX RWL-160 (ethoxylated hydrogenated castor oil laurate: product name of Nihon Emulsion Co., Ltd.).

As the present nonionic surfactant, ethoxylated castor oil or ethoxylated hydrogenated castor oil is preferable. Among ethoxylated castor oil or ethoxylated hydrogenated castor oil, those having a hydrophile-lipophile balance (so-called HLB) in the range from 9.0 to 20.0 are suitable, and those having the HLB around 14.0 are particularly suitable.

A content amount of the present nonionic surfactant in the present invention is usually in the range from 0.5 to 4% by weight and preferably in the range from 1 to 3% by weight in the composition of the present invention.

Water in the present invention may be either of so-called soft water or hard water, and ion-exchanged water, distilled water or the like may be also used. Water having an electric conductivity of 2 μs/cm or less and an electric resistance of 0.5 MΩ or more is preferably used.

A content amount of water in the present invention is usually in the range from 25 to 85% by weight in the composition of the present invention.

The composition of the present invention is usually an oil-in-water emulsion, and a weight ratio of pyriproxyfen and water in the composition of the present invention is in the range from 1:20 to 1:3, and is preferably in the range from 1:15 to 1:5.

The composition of the present invention contains pyriproxyfen, the present hydrophobic organic solvent, polyvinyl alcohol, the present nonionic surfactant, and water as essential components but, if it is necessary, it may contain a surfactant except for the present nonionic surfactant, a viscosity adjusting agent, a anti-foaming agent, an antifreezing agent, an antiseptic agent, a stabilizing agent, a coloring agent, a perfume, an effectiveness enhancing agent, a harmful medicine effect reducing agent, and the like.

Examples of the surfactant except for the present nonionic surfactant include a nonionic surfactant such as polyoxyethylene glycerine fatty acid ester, polyoxyethylene sorbitan fatty acid ester, polyoxyethylene alkyl ether, polyoxyethylene alkylphenyl ether, polyoxyethylene alkylphenyl ether/formalin condensate, ethylene oxide/propylene oxide/block polymer and the like, and an anionic surfactant such as alkyl sulfate, polyoxyethylene alkyl ether sulfate, polyoxyethylene alkylphenyl ether sulfate, polyoxystyryl phenyl ether sulfate, dialkyl sulfosuccinate, alkylbenzene sulfonate, monoalkylnaphthalene sulfonate, dialkylnaphthalene sulfonate, naphthalene sulfonate/formalin condensate, alkyldiphenyl ether disulfonate, polyoxyethylene aklylphenyl ether sulfonate and the like.

Examples of the viscosity adjusting agent include a natural polysaccharide such as xanthan gum, lumthan gum, roast bean gum, guar gum, carrageenan, welan gum, alginic acid, alginate, tragacanth gum and the like; a synthetic polymer such as sodium polyacrylate and the like; a semi-synthetic polymer such as carboxymethylcellulose and the like; a mineral powder such as aluminum silicate, magnesium aluminum silicate, smectite, bentonite, heclite, synthetic silicate hydrate, dried silica and the like; and alumina sol. Such the viscosity adjusting agent which is commercially available may be used as it is, and as xanthan gum, for example, Kelthan S (product name of Monsant, Corp.) may be listed, as aluminum silicate, for example, Beagum R (product name of Vanderbilt, Co., Ltd.) may be listed, as dried silica, for example, Aerozil 200 (product name of Degussa-Huels AG) may be listed, as the mixture of dried silica and aluminum sol, for example, Aerozil COK-84 (product name of Degussa-Huels AG) may be listed. In the case where the viscosity adjusting agent is used, a content amount thereof is usually in the range from 0.01 to 10% by weight, and preferably in the range from 0.1 to 5% by weight in the composition of the present invention.

Examples of the anti-foaming agent include a silicone-based anti-foaming agent such as Antifoam C (product name of Dow Corning Ltd.), Antifoam CE (product name of Dow Corning Ltd.), TSA 730 (product name of Toshiba Silicone Co., Ltd.), TSA 731 (product name of Toshiba Silicone Co., Ltd.), TSA 732 (product name of Toshiba Silicone Co., Ltd.), YMA 6509 (product name of Toshiba Silicone Co., Ltd.) and the like; and a fluorine-based anti-foaming agent such as Fluowet PL 80 (product name of Clariant Ltd.) and the like. In the case where the anti-foaming agent is used, a content amount thereof is usually in the range from 0.001 to 3% by weight in the composition of the present invention.

Examples of the antifreezing agent include a water soluble glycol such as ethylene glycol, propylene glycol and the like. In the case where the antifreezing agent is used, a content amount thereof is usually in the range from 0.5 to 30% by weight, preferably in the range from 1 to 20% by weight, and more preferable in the range from 5 to 10% by weight in the composition of the present invention.

Examples of the antiseptic agent include p-hydroxybenzoic acid ester, salicylic acid derivative, isothiazolin-3-on derivative (for example, Biohope L (product name of K.I. Chemical Industry Co., Ltd.) and the like. In the case where the antiseptic agent is used, a content amount thereof is usually in the range from 0.01 to 5% by weight, preferably in the range from 0.05 to 3% by weight, and more preferably in the range from 0.1 to 1% by weight in the composition of the present invention.

The composition of the present invention can be manufactured, for example, by the following method.

A uniform oil phase solution containing pyriproxyfen is prepared by mixing pyriproxyfen, the present hydrophobic organic solvent and the present nonionic surfactant, if it is necessary, with heating. Separately, an aqueous phase solution containing polyvinyl alcohol is prepared by mixing polyvinyl alcohol and water, if it is necessary, further adding the anti-foaming agent. Next, the composition of the present invention is manufactured by emulsifying and dispersing the oil phase solution and the aqueous phase solution. If it is necessary, the above-described viscosity adjusting agent, antifreezing agent, antiseptic agent, stabilizing agent and coloring agent may be further added to the manufactured composition of the present invention.

As a method of emulsifying and dispersing, for example, a mechanically dispersing method of forcefully dispersing by applying mechanical energy is intended.

Examples of the mechanically dispersing method include a method of forcefully emulsifying and dispersing a pyriproxyfen solution into water by high mechanical sharing force. Examples of a dispersing machine giving a high sharing force used in this method include a machine which agitates the mixture of pyriproxyfen solution and polyvinyl alcohol aqueous solution at a high speed (for example, planetary agitating machine, homomixer), a machine which inject the mixture into water at a high speed from a pore to impact into a plate (for example, Gaulin homogenizer, microfluidizer), a machine which disperses the mixture by the sharing force generated upon forcefully passing through a narrow clearance (for example, colloid mill), or a dispersing machine which utilizes supersonic wave and the like, and they may be utilized. The dispersing machine used in the present invention may be selected by totally considering the easiness of dispersion of the mixture, the viscosity of a system, adaptability with all of the steps, a product amount and the like.

To the composition of the present invention obtained via the emulsification and dispersion step, water may be added so that the composition is properly diluted, and to water which is added, the surfactant except for the present nonionic surfactant, the viscosity adjusting agent, the anti-foaming agent, the antifreezing agent, the antiseptic agent, the stabilizing agent, the coloring agent, the perfume, the effectiveness enhancing agent, the harmful effect of a medicine reducing agent, and the like may be added.

The composition of the present invention is a composition in which oil droplets have been uniformly dispersed in an aqueous continuous phase. In the present invention, from the viewpoints of preparation stability during the long term storage and the like, a condition of emulsifying and dispersing is selected so that the volume median diameter of the oil droplet particle becomes preferably in the range from 0.1 to 7 µm, more preferably in the range from 0.5 to 5 µm, and still more preferably in the range from 1 to 3 µm.

The volume median diameter of the oil droplet particle in the composition of the present invention is a value calculated by analyzing an image of a large number of particles measured by laser beam diffraction scattering based on a Mie-scattering theory, and as a specific measuring machine, Master Sizer 2000 (product name of Malburn Co., Ltd.) may be listed. A particle size distribution measured by a device is a particle size distribution based on a particle volume when the particle measured is supposed to be in a spherical shape and, therefore, the volume median diameter (VMD) in the present specification indicates the value in which a total volume of the particles having a value smaller than this value and a total volume of the particles having a value larger than this value occupy 50% of the whole volume, respectively.

Examples of an insect pest to which the composition of the present invention exerts an effect of control include the followings:

Hemiptera Insect Pests:
planthoppers such as small brown planthopper (*Laodelphax striatellus*), brown planthopper (*Nilaparvata lugens*), whitebacked rice planthopper (*Sogatella furcifera*) and the like, leafhoppers such as green rice leafhopper (*Nephotettix cincticeps*), Taiwan green rice leafhopper (*Nephotettix virescens*) and the like, aphides such as cotton aphid (*Aphis gossypii*), green peach aphid (*Myzus persicae*), apple aphid (*Aphis citricola*), turnip aphid (*Lipaphis pserudobrassicae*), pear green aphid (*Nippolachnus piri*), black citrus aphid (*Toxoptera aurantil*), tropical citrus aphid (*Toxoptera citricidius*) and the like, stink bugs such as green stink bug (*Nezara antennata*), *Cletus punctiger*, bean bug (*Riptortus clavatus*), brownwinged green bug (*Plautia stali*) and the like, whiteflies such as greenhouse whitefly (*Trialeurodes vaporariorum*), sweetpotato whitefy (*Bemisia tabaci*), silverleaf whitefly (*Bemisia argentifolii*) and the like, scale insects such as California red scale (*Aonidiella aurantii*), San Jose scale (*Comstockaspis perniciosa*), citrus snow scale (*Unaspis citri*), white peach scale (*Pseudaulacaspis pentagona*), brown olive scale (*Saissetia oleae*), purple scale (*Lepidosaphes beckii*), red wax scale (*Ceroplastes rubens*), cottonycushion scale (*Icerya purchasi*) and the like, lace bugs, jumping plant louses and the like;
Lepidopteran Insect Pests:
Pyralidae such as rice stem borer (*Chilo suppressalis*), rice leafroller (*Cnaphalocrocis medinalis*), European corn borer (*Ostrinia nubilalis*), cabbage webworm (*Hellulla undalis*), bluegrass webworm (*Parapediasia teterrella*), cotton leafroller (*Notarch derogata*), Indian meal moth (*Plodia interpuncterlla*) and the like, Noctuidae such as tabaco cutworm (*Spodoptera litura*), rice armyworm (*Pseudaletia separata*), cabbage armyworm (*Mamestra brassicae*), black cutworm (*Agrotis ipsilon*), *Trichoplusia* spp., *Heliothis* spp., *Helicoverpa* spp. and the like, Pieridae such as small white (*Pieris rapae*) and the like, Tortricidae such as *Adoxophyes* spp., oriental fruit moth (*Grapholita molesta*), codling moth (*Cydia pomonella*) and the like, Carposinidae such as peach fruit moth (*Carposina niponensis*) and the like, Lyonetiidae such as *Lyonetia* spp. and the like, Lymantriidae such as *Lymantria* spp., *Euproctis* spp. and the like, Yponomeutidae such as diamondback moth (*Plutela xylostella*) and the like, Gelechiidae such as pink ball worm (*Pectinophora gossypiella*) and the like, Arctiidae such as fall webworm (*Hyphantria cunea*) and the like, Tineidae such as casemaking clothes moth (*Tinea translucens*), webbing clothes moth (*Tineola bisselliella*) and the like;
Diptera Insect Pests:
*Culex* spp. such as common mosquito (*Culex pipiens pallens*), oriental latrine fly (*Culex tritaeniorhynchus*) and the like, *Aedes* spp. such as dengue mosquito (*Aedes aegypti*), tiger mosquito (*Aedes albopictus*) and the like, *Anopheles* spp. such as chinese malaria mosquito (*Anopheles sinensis*) and the like, Chironomidae, Muscidae such as housefly (*Musca domestica*), false stablefly (*Muscina stabulans*) and the like, Calliphoridae, Sarcophagidae, little housefly (*Fannia canicularis*), Anthomyiidae such as seedcorn maggot (*Delia platura*), onion maggot (*Delia antiqua*) and the like, leaf miner flies such as legume leafminer (*Liriomyza trifolii*) and the like, fruit flies, Phoridae, *Drosophila*, moth flies, Simuliidae (*blackfly*), gadflies, and *Culicoides* and the like;
Coleopteron Insect Pests:
Corn root worms such as Western corn room worm (*Diabrotica virgifera virgifera*), Southern corn root worm (*Diabrotica undecimpunctata howardi*) and the like, gold beetles such as cupreous chafer (*Anomala cuprea*), soybean beetle (*Anomala rufocuprea*) and the like, weevils such as maize weevil (*Sitophilus zeamais*), ricewater weevil (*Lissorhoptrus oryzophilus*), alfalfa weevil (*Hypera pastica*), adzuki bean weevil (*Callosobruchuys chienensis*) and the like, Tenebrionidae such as yellow mealworm (*Tenebrio molitor*), red flour beetles (*Tribolium castaneum*) and the like, Chrysomelidae such as cucurbit leaf beetle (*Aulacophora femoralis*), striped flea beetle (*Phyllotreta striolata*), Colorado beetle (*Leptinotarsa decemlineata*) and the like, *Epilachna* such as twentyeight-spotted ladbirds (*Epilachna vigintioctopunctata*) and the like, Bostrychidae, robe beetle (*Paederus fuscipes*) and the like;
Thysanopteran Insect Pests:
melon thrips (*Thrips palmi*), onion thrips (*Thrips tabaci*), flower thrips (*Thrips hawaiiensis*), yellow tea thrips (*Scirtothrips dorsalis*), flower thrips (*Frankliniella intonsa*), western flower thrips (*Frankliniella occidentalis*), *Ponticulothrips diospyrosi* and the like;
Hymenopteran Insect Pests:
ants, hornets, Bethylidae, sawflies such as cabbage sawfly (*Athalia japonica*) and the like.

When the pesticidal composition containing pyriproxyfen in the present invention is sprayed, an amount thereof may be varied depending upon a variety of conditions such as weather conditions, application period, application methods, soil conditions, subject crops, subject pests and the like, however, usually, the pesticidal composition is applied by diluting it with water so that an amount of pyriproxyfen becomes in the range from 0.1 to 1,000 g/1000 m$^2$ and preferably in the range from 1 to 100 g/1000 m$^2$. Such an application or spraying amount may be varied depending upon a situation such as application times, application places, application methods, kinds of pests, degrees of crop damage and the like, regardless of the above-described range, and the amount may be increased and decreased.

Moreover, the present composition which has been diluted with water for spraying may be also sprayed in air, for example, from helicopters, airplanes or radio controlled helicopters.

EXAMPLES

Hereinafter, the present invention will be described below in detail by Manufacturing Examples and Experimental Examples, however, the present invention is not limited thereto. It should be noted that in the following Examples, the term "part(s)" denotes part(s) by weight.

Manufacturing Example 1

An oil phase solution was prepared by dissolving 10 parts by weight of pyriproxyfen into 20 parts by weight of a mixture of 1-phenyl-1-xylylethane and 1-phenyl-1-ethylphenylethane (Hisol SAS-296, product name of Nippon Oil Co., Ltd.) and further, by adding and dissolving 2.5 parts by weight of ethylene oxide/propylene oxide block polymer (Pepol B-184, HLB=10.1, product name of Toho Chemical Industry Co., Ltd.) and 2.5 parts by weight of ethoxylated castor oil (Sorpol CA42, HLB=13.3, product name of Toho Chemical Industry Co., Ltd.) into the mixture.

Separately from the above-described oil phase solution, a polyvinyl alcohol aqueous solution was prepared by dissolving 2.0 parts by weight of polyvinyl alcohol (GOHSENOL GL-05, surface tension of 1% by weight of aqueous solution: 45 dyne/cm, viscosity of 4% aqueous solution at 20° C.: 4.8-5.8 mPa·s, degree of saponification; 86.5-89.0%, product name of Nippon Synthetic Chemical Industries, Co., Ltd.) into 18 parts by weight of water.

An oil-in-water emulsion was obtained by adding 20 parts by weight of the above-described polyvinyl alcohol aqueous solution to 35 parts by weight of the above-described oil phase solution, agitating it for 5 minutes at 6000 rpm by a T.K. autohomomixer (homogenizer, manufactured by Tokushu Kika Kogyo, Co., Ltd.) to emulsify and disperse it. 5 parts by weight of propylene glycol was added to the obtained oil-in-water emulsion and, further, 40 parts by weight of water was added to make a total amount of the composition into 100 parts by weight and, then, Composition 1 of the present invention was obtained.

Manufacturing Example 2

A uniform oil phase solution was prepared by placing 10.1 parts by weight of pyriproxyfen previously heated and melt, 20 parts by weight of a mixture of 1-phenyl-1-xylylethane and 1-phenyl-1-ethylphenylethane (Hisol SAS-296, product name of Nippon Oil Co., Ltd.), and 2 parts by weight of ethoxylated castor oil (Alkamulus OR/40, HLB=14, product name of Rhodia Corp.) in a container and agitating it by a magnetic stirrer for one hour at 25° C.

A uniform 6.25% polyvinyl alcohol aqueous solution was prepared by putting 29.8 parts by weight of water, 0.2 parts by weight of the anti-foaming agent (Antifoam C, product name of Dow Corning Asia, Corp.) and 2 parts by weight of polyvinyl alcohol (GOHSENOL GL-05, surface tension of 1% by weight of aqueous solution: 45 dyne/cm, viscosity of 4% aqueous solution at 20° C.: 4.8-5.8 mPa·s, degree of saponification; 86.5-89.0%, product name of Nippon Synthetic Chemicals Co., Ltd.) into another container, and agitating it by Three One Motor (agitator manufactured by Yamato Scientific Co., Ltd.) at 300 rpm for one hour after the temperature was raised to 60° C.

An oil-in-water emulsion was obtained by adding 32.1 parts by weight of the above-described oil phase solution to 32 parts by weight of the above-described 6.25% polyvinyl alcohol aqueous solution, agitating it by the T.K. autohomomixer (homogenizer, manufactured by Tokushu Kika Kogyo Co., Ltd.) at 6000 rpm for 10 minutes at 25° C. to emulsify and disperse it. 5 parts by weight of propylene glycol and, then, 26.6 parts by weight of an aqueous solution containing 0.2 parts by weight of xanthan gum, 0.4 parts by weight of aluminum silicate and 0.2 parts by weight of Proxycel GXL (20% propylene glycol aqueous solution of 1,2-benzisothiazoline-3-on, product name of Avecia KK) were added to the obtained oil-in-water emulsion and, further, 6.3 parts by weight of water was added and, then, Composition 2 of the present invention was obtained.

The volume median diameter of the oil droplet was 1.5 μm in Composition 2 of the present invention (measurement by Master Sizer 2000, manufactured by Malburn Co., Ltd.) and the viscosity was 1940 mPa·s (when a B type viscosity meter with a No. 2 rotor at 6 rpm is used, 25° C.).

Manufacturing Example 3

Composition 3 of the present invention was obtained by preparing similarly to Manufacturing Example 2 except that 2 parts by weight of ethoxylated castor oil (Alkamulus OR/40, HLB=14, product name of Rhodia Co, Ltd.) of Manufacturing Example 2 was changed to 2 parts by weight of ethoxylated castor oil (Alkamulus R81, HLB=9.2, product name of Rhodia Co., Ltd.).

The volume median diameter of the oil droplet was 1.4 μm in Composition 3 of the present invention (measurement by Master Sizer 2000, manufactured by Malburn Co., Ltd.).

Manufacturing Example 4

Composition 4 of the present invention was obtained by preparing similarly to Manufacturing Example 2 except that 2 parts by weight of ethoxylated castor oil (Alkamulus OR/40, HLB=14, product name of Rhodia Co., Ltd.) of Manufacturing Example 2 was changed to 2 parts by weight of ethoxylated castor oil (Alkamulus BR, HLB=12.6, product name of Rhodia Co., Ltd.).

The volume-median diameter of the oil droplet was 1.6 μm in Composition 4 of the present invention (measurement by Master Sizer 2000, manufactured by Malburn Co., Ltd.).

Manufacturing Example 5

Composition 5 of the present invention was obtained by preparing similarly to Manufacturing Example 2 except that 2 parts by weight of ethoxylated castor oil (Alkamulus OR/40, HLB=14, product name of Rhodia Co., Ltd.) of Manufacturing Example 2 was changed to 2 parts by weight of ethoxylated castor oil (Sorpol CA42, HLB=13.3, product name of Toho Chemical Industry Co., Ltd.).

The volume median diameter of the oil droplet was 1.5 μm in Composition 5 of the present invention (measurement by Master Sizer 2000, manufactured by Malburn Co., Ltd.).

Manufacturing Example 6

Composition 6 of the present invention was obtained by preparing similarly to Manufacturing Example 2 except that 2 parts by weight of ethoxylated castor oil (Alkamulus OR/40, HLB=14, product name of Rhodia Co., Ltd.) of Manufacturing Example 2 was changed to 2 parts by weight of ethoxylated castor oil (Alkamulus 14R, HLB=14.9, product name of Rhodia Co., Ltd.).

The volume median diameter of the oil droplet was 1.6 μm in Composition 6 of the present invention (measurement by Master Sizer 2000, manufactured by Malburn Co., Ltd.).

Manufacturing Example 7

Composition 7 of the present invention was obtained by preparing similarly to Manufacturing Example 2 except that 20 parts by weight of the mixture of 1-phenyl-1-xylylethane and 1-phenyl-1-ethylphenylethane (Hisol SAS-296, product name of Nippon Oil Co., Ltd.) of Manufacturing Example 2 was changed to 20 parts by weight of aromatic hydrocarbon solvent (Solvesso 200, product name of ExxonMobil Co., Ltd.).

The volume median diameter of the oil droplet was 1.1 μm in Composition 7 of the present invention (measurement by Master Sizer 2000, manufactured by Malburn Co., Ltd.).

Manufacturing Example 8

Composition 8 of the present invention was obtained by preparing exactly similar to Manufacturing Example 2 except that 2 parts by weight of xanthan gum and 4 parts by weight of aluminum silicate of Manufacturing Example 2 were changed to 1.4 parts by weight of xanthan gum and 2.8 parts by weight of aluminum silicate.

The volume median diameter of the oil droplet was 1.5 μm in Composition 8 of the present invention (measurement by Master Sizer 2000, manufactured by Malburn Co., Ltd.) and the viscosity was 1210 mPa·s (when a B type viscosity meter with a No. 2 rotor at 6 rpm was used, 25° C.).

Manufacturing Example 9

Composition 9 of the present invention was obtained by preparing exactly similar to Manufacturing Example 1 except that 45 parts by weight of water was added instead of 5 parts by weight of propylene glycol and 40 parts by weight of water.

Next, Manufacturing Examples of Comparative compositions will be described below.

Comparative Manufacturing Example 1

An oil phase solution was prepared by dissolving 10 parts by weight of pyriproxyfen into 20 parts by weight of the mixture of 1-phenyl-1-xylylethane and 1-phenyl-1-ethylphenylethane (Hisol SAS-296, product name of Nippon Oil Co., Ltd.) and, further, by adding and dissolving 2.5 parts by weight of ethylene oxide/propylene oxide block polymer (Pepol B-184, HLB=10.1, product name of Toho Chemical Industry Co., Ltd.) and 2.5 parts by weight of ethoxylated castor oil (Sorpol CA42, HLB=13.3, product name of Toho Chemical Industry Co., Ltd.).

An oil-in-water emulsion was obtained by adding 20 parts by weight of water to the above-described oil phase solution and by agitating it by the T.K. autohomomixer (homogenizer, manufactured by Tokushu Kika Kogyo, Co., Ltd.) at 6000 rpm for 5 minutes to emulsify and disperse it. 5 parts by weight of propylene glycol was added to the obtained oil-in-water emulsion and, further, 40 parts by weight of water was added so that a total amount was made into 100 parts by weight, and Comparative composition 1 of the present invention was obtained.

Comparative Manufacturing Example 2

Comparative composition 2 of the present invention was obtained by preparing similarly to Manufacturing Example 2 except that 2 parts by weight of ethoxylated castor oil (Alkamulus OR/40, HLB=14, product name of Rhodia Co., Ltd.) of Manufacturing Example 2 was not added and, further, that 2 parts by weight of polyvinyl alcohol (GOHSENOL GL-05: product name of Nippon Synthetic Chemical Industry Co., Ltd.) was changed to 4 parts by weight of polyvinyl alcohol (GOHSENOL GL-05: product name of Nippon Synthetic Chemical Industry Co., Ltd.).

The volume median diameter of the oil droplet was 3.2 μm in Comparative composition 2 of the present invention (measurement by Master Sizer 2000, manufactured by Malburn Co., Ltd.) and the viscosity of Comparative composition 2 was 1890 mPa·s (when a B type viscosity meter with a No. 2 rotor at 6 rpm was used, 25° C.)

Comparative Manufacturing Example 3

Comparative composition 3 of the present invention was obtained by preparing similarly to Manufacturing Example 2 except that 2 parts by weight of ethoxylated castor oil (Alkamulus OR/40, HLB=14, product name of Rhodia Co., Ltd.) of Manufacturing Example 2 was changed to 2 parts by weight of polyoxyethylene tristyrylphenyl ether (Soprophor CY8, HLB=13.7, product name of Rhodia Co., Ltd.).

The volume median diameter of the oil droplet was 2.0 μm in Comparative composition 3 of the present invention (measurement by Master Sizer 2000, manufactured by Malburn Co., Ltd.) and the viscosity of Comparative composition 3 was 1900 mPa·s Ashen a B type viscosity meter with a No. 2 rotor at 6 rpm was used, 25° C.)

Comparative Manufacturing Example 4

Comparative composition 4 of the present invention was obtained by preparing similarly to Manufacturing Example 2 except that 2 parts by weight of ethoxylated castor oil (Alkamulus OR/40, HLB=14, product name of Rhodia Co., Ltd.) of Manufacturing Example 2 was changed to 2 parts by weight of polyoxyethylene nonylphenol (Igepar CO-720, HLB=13.6, product name of Rhodia Co., Ltd.).

The volume median diameter of the oil droplet was 1.5 μm in Comparative composition 4 (measurement by Master Sizer 2000, manufactured by Malburn Co., Ltd.) and the viscosity of Comparative composition 4 was 1940 mPa·s (when a B type viscosity meter with a No. 2 rotor at 6 rpm was used, 25° C.)

Comparative Manufacturing Example 5

Comparative composition 5 of the present invention was obtained by preparing similarly to Manufacturing Example 2 except that 2 parts by weight of ethoxylated castor oil (Alkamulus OR/40, HLB=14, product name of Rhodia Co., Ltd.) of Manufacturing Example 2 was changed to 2 parts by weight of polyoxyethylene sorbitan ester (Alkamulus T20, HLB=16.7, product name of Rhodia Co., Ltd.).

The volume median diameter of the oil droplet was 1.6 μm in Comparative composition 5 (measurement by Master Sizer 2000, manufactured by Malburn Co., Ltd.) and the viscosity of Comparative composition 5 was 1900 mPa·s (when a B type viscosity meter with a NO. 2 rotor at 6 rpm was used, 25° C.).

Comparative Manufacturing Example 6

Comparative composition 6 was obtained by preparing similarly to Manufacturing Example 2 except that 2 parts by weight of ethoxylated castor oil (Alkamulus OR/40, HLB=14, product name of Rhodia Co., Ltd.) of Manufacturing Example 2 was changed to 2 parts by weight of polyoxyethylene sorbitan monolauric acid ester (Sorbon T20, HLB=13.6, product name of Toho Chemical Industry Co., Ltd.).

The volume median diameter of the oil droplet was 1.5 μm in Comparative composition 6 (measurement by Master Sizer 2000, manufactured by Malburn Co., Ltd.) and the viscosity of Comparative composition 6 was 1940 mPa·s (when a B type viscosity meter with a No. 2 rotor at 6 rpm was used, 25° C.).

Experimental Example 1

Each 100 g of Composition 1 of the present invention and Comparative composition 1 was separately placed in a container made of HDPE, and the container was tightly sealed. The container was stored under a condition that a cycle of leaving the container at −15° C. for 3 days and at 30° C. for 4 days was alternately repeated. The appearance of the composition after a predetermined period was visually observed and a ratio of a transparent aqueous phase in the composition was examined. The results are indicated in Table 1.

TABLE 1

|  | After 2 weeks |
|---|---|
| Composition 1 of the present invention | Extremely trace amount |
| Comparative composition 1 | 44% |

The composition of the present invention is excellent in storage stability since even in the case where it is stored under the condition of repetition of low and high temperatures, there is little separation between an aqueous phase and an oil phase.

Experimental Example 2

Each 100 g of Compositions 1, 9 and Comparative composition 3 was separately placed in the container made of HDPE, and the container was tightly sealed. The container was stored under the condition that a cycle of leaving the container at −15° C. for 3 days and at 30° C. for 4 days was alternately repeated. The appearance and the ratio of phase separation in the composition after two weeks were examined. The results are indicated in Table 2.

TABLE 2

|  | Appearance | Degree of separation (%) |
|---|---|---|
| Composition 1 of the present invention | No change | 0 |
| Composition 7 of the present invention | Slight separation of aqueous phase | Trace |
| Comparative composition 3 | Separation of aqueous phase at upper portion | 10 |

Experimental Example 3

Each 100 g of Compositions 2-8 of the present invention and Comparative compositions 2-6 was separately placed in the container made of HDPE, and the container was tightly sealed. The container was stored at 54° C. After the predetermined period, the volume median diameter of the oil droplet particle in the composition was measured by Master Sizer 2000 manufactured by Malburn Co., Ltd. The results are indicated in Table 3.

TABLE 3

|  | Before storage (μm) | After 2 weeks (μm) |
|---|---|---|
| Composition 2 of the present invention | 1.5 | 1.4 |
| Composition 3 of the present invention | 1.4 | 1.3 |
| Composition 4 of the present invention | 1.6 | 1.5 |
| Composition 5 of the present invention | 1.5 | 1.4 |
| Composition 6 of the present invention | 1.6 | 1.5 |
| Composition 7 of the present invention | 1.1 | 1.1 |
| Composition 8 of the present invention | 1.5 | 1.5 |
| Comparative composition 2 | 3.2 | 6.2 |
| Comparative composition 3 | 2.0 | 9.5 |
| Comparative composition 4 | 1.5 | 6.4 |
| Comparative composition 5 | 1.6 | 3.6 |
| Comparative composition 6 | 1.7 | 5.1 |

The composition of the present invention is excellent in storage stability since even in the case of the storage under the condition of high temperature, the particle size of the liquid droplet particle in the oil phase is scarcely increased.

Experimental Example 4

The appearance and the ratio of phase separation of the compositions after 3 months storage at 40° C. were observed. The results are indicated in Table 4.

TABLE 4

|  | Appearance | Ratio of phase separation (%) |
|---|---|---|
| Composition 1 of the present invention | No change | 0 |
| Composition 2 of the present invention | Extremely trace amount of aqueous phase separation | 1> |
| Composition 3 of the present invention | No change | 0 |
| Composition 4 of the present invention | No change | 0 |
| Composition 5 of the present invention | No change | 0 |
| Composition 6 of the present invention | No change | 0 |
| Composition 7 of the present invention | No change | 0 |
| Comparative composition 1 | Separation of aqueous phase at upper portion | 5 |
| Comparative composition 2 | Separation of aqueous phase at upper portion | 15 |
| Comparative composition 4 | Separation of aqueous phase at upper portion | 10 |
| Comparative composition 5 | Separation of aqueous phase at upper portion | 5 |
| Comparative composition 6 | Separation of aqueous phase at upper portion | 5 |

What is claimed is:

1. A pesticidal composition consisting essentially of
   (a) 4-phenoxyphenyl 2-(2-pyridyloxy)propyl ether,
   (b) a hydrophobic organic solvent capable of dissolving 0.1-fold by weight of 4-phenoxyphenyl 2-(2-pyridyloxy)propyl ether at 0° C.,
   (c) polyvinyl alcohol,
   (d) a nonionic surfactant selected from the group consisting of alkoxylated castor oil, alkoxylated hydrogenated castor oil and alkoxylated hydrogenated castor oil fatty acid ester, and
   (e) water,
   wherein a weight ratio of (a) 4-phenoxyphenyl 2-(2-pyridyloxy)propyl ether and (e) water is in the range from 1:20 to 1:3,
   content amounts of (b) the hydrophobic organic solvent, (c) polyvinyl alcohol, (d) the nonionic surfactant, and (e) water are in the range from 5 to 30% by weight, from 0.5 to 4% by weight, from 0.5 to 4% by weight, and from 25 to 85% by weight, respectively, and
   a ratio of separation of the pesticidal composition after 3 months storage at 40° C. is 1% or less.

2. The pesticidal composition according to claim 1, wherein content amounts of (b) the hydrophobic organic solvent, (c) polyvinyl alcohol, (d) the nonionic surfactant, and (e) water are in the range from 10 to 20% by weight, from 1 to 3% by weight, from 1 to 3% by weight, and from 25 to 85% by weight, respectively.

3. The pesticidal composition according to claim 1, wherein the weight ratio of (a) 4-phenoxyphenyl 2-(2-pyridyloxy)propyl ether and (e) water is in the range from 1:15 to 1:5.

4. The pesticidal composition according to claim 3, wherein content amounts of (b) the hydrophobic organic solvent, (c) polyvinyl alcohol, (d) the nonionic surfactant, and (e) water are in the range from 10 to 20% by weight, from 1 to 3% by weight, from 1 to 3% by weight, and from 25 to 85% by weight, respectively.

5. The pesticidal composition according to claim 1, wherein (b) the hydrophobic organic solvent is an aromatic hydrocarbon solvent.

6. The pesticidal composition according to claim 2, wherein (b) the hydrophobic organic solvent is an aromatic hydrocarbon solvent.

7. The pesticidal composition according to claim 3, wherein (b) the hydrophobic organic solvent is an aromatic hydrocarbon solvent.

8. The pesticidal composition according to claim 4, wherein (b) the hydrophobic organic solvent is an aromatic hydrocarbon solvent.

9. The pesticidal composition according to claim 3, wherein content amounts of (b) the hydrophobic organic solvent, (c) polyvinyl alcohol, (d) the nonionic surfactant, and (e) water are in the range from 10 to 20% by weight, from 0.5 to 4% by weight, from 0.5 to 4% by weight, and from 25 to 85% by weight, respectively.

10. A pesticidal composition consisting essentially of
(a) 4-phenoxyphenyl 2-(2-pyridyloxy)propyl ether,
(b) a hydrophobic organic solvent capable of dissolving 0.1-fold by weight of 4-phenoxyphenyl 2-(2-pyridyloxy)propyl ether at 0° C.,
(c) polyvinyl alcohol,
(d) a nonionic surfactant selected from the group consisting of alkoxylated castor oil, alkoxylated hydrogenated castor oil and alkoxylated hydrogenated castor oil fatty acid ester, and
(e) water,
wherein a weight ratio of (a) 4-phenoxyphenyl 2-(2-pyridyloxy)propyl ether and (e) water is in the range from 1:20 to 1:3,
content amounts of (b) the hydrophobic organic solvent, (c) polyvinyl alcohol, (d) the nonionic surfactant, and (e) water are in the range from 5 to 30% by weight, from 0.5 to 4% by weight, from 0.5 to 4% by weight, and from 25 to 85% by weight, respectively,
the pesticidal composition is an oil-in-water emulsion, and
a ratio of separation of the pesticidal composition after 3 months storage at 40° C. is 1% or less.

11. The pesticidal composition according to claim 10, wherein the weight ratio of (a) 4-phenoxyphenyl 2-(2-pyridyloxy)propyl ether and (e) water is in the range from 1:15 to 1:5.

12. The pesticidal composition according to claim 10, wherein (d) the nonionic surfactant is alkoxylated castor oil.

13. The pesticidal composition according to claim 10, wherein (d) the nonionic surfactant is ethoxylated castor oil.

14. The pesticidal composition according to claim 10, wherein the (c) polyvinyl alcohol:
has a content of 4% by total weight of the pesticidal composition,
has a viscosity in the range from 1 to 70 mPa at 20° C., and
has a degree of saponification in the range from 70 to 100% by mole.

* * * * *